United States Patent
Smith et al.

[11] Patent Number: 5,430,214
[45] Date of Patent: Jul. 4, 1995

[54] HYDRODEHALOGENATION PROCESS AND CATALYST FOR USE THEREIN

[75] Inventors: David D. Smith; Michael T. Holbrook; A. Dale Harley, all of Baton Rouge, La.; Larry N. Ito, Midland, Mich.

[73] Assignee: The Dow Chemical Company, Midland, Mich.

[21] Appl. No.: 153,557

[22] Filed: Nov. 16, 1993

Related U.S. Application Data

[63] Continuation of Ser. No. 955,215, Oct. 1, 1992, abandoned.

[51] Int. Cl.$^6$ .............................. C07C 1/26
[52] U.S. Cl. .................... 585/641; 585/642; 502/325
[58] Field of Search .......... 585/641, 642; 502/325; 570/189, 216, 220, 230

[56] References Cited

U.S. PATENT DOCUMENTS

| | | | |
|---|---|---|---|
| 2,379,697 | 7/1945 | Evans et al. | 260/680 |
| 3,892,818 | 7/1975 | Scharfe et al. | 260/676 R |
| 4,818,368 | 4/1989 | Kalnes et al. | 208/50 |
| 4,899,001 | 2/1990 | Kalnes et al. | 585/310 |
| 5,013,424 | 5/1991 | James, Jr. et al. | 208/78 |

FOREIGN PATENT DOCUMENTS

| | | |
|---|---|---|
| 4012007 | of 0000 | Germany . |
| 235630 | 5/1986 | Germany . |
| 3510034 | 9/1986 | Germany . |

*Primary Examiner*—Asok Pal
*Assistant Examiner*—P. Achutamurthy

[57] ABSTRACT

A hydrodehalogenation process, comprising the step of reacting a saturated halohydrocarbon (e.g., 1,2-dichloropropane) with hydrogen or a hydrogen donor in the gas phase in the presence of a catalytically effective amount of ruthenium on a support, and at temperatures of at least about 100 degrees Celsius, to produce reaction products including a corresponding non-halogenated, unsaturated hydrocarbon (e.g., propylene).

14 Claims, 2 Drawing Sheets

0.5% Ruthenium on Alumina

— PDC Conversion    —+— P-pene/P-pane Select 0.5% Ruthenium on Alumina  300 C

HYDRODEHALOGENATION PROCESS AND CATALYST FOR USE THEREIN

This application is a continuation of prior application Ser. No. 07/955,215, filed Oct. 1, 1992, now abandoned.

The present invention relates to hydrodehalogenation catalysts and associated catalytic processes, and more particularly to processes for converting saturated halohydrocarbons to corresponding non-halogenated, unsaturated hydrocarbons.

One saturated halohydrocarbon of particular interest is 1,2-dichloropropane (hereafter, PDC). PDC is formed in substantial quantities as a by-product in the commercial production of propylene oxide by the propylene-chlorohydrin method. Disposal of PDC is an increasingly difficult and expensive proposition, and heretofore it has proven difficult also to find productive ways of using the by-product PDC material.

At least some attempts have been made to catalytically convert PDC to propylene (a corresponding non-halogenated and unsaturated hydrocarbon) plus other useful materials such as hydrochloric acid. In German Patent Publication No. 235,630 A1 (DE '630), for example, PDC is converted to propylene in a catalytic gas phase reaction at temperatures ranging from 170 degrees Celsius to 450 degrees Celsius. The catalyst is described as an activated carbon which has been treated with a suspension of iron oxides and/or iron oxide hydrates, and then dried at temperatures in the range of 80 degrees to 200 degrees Celsius.

Other methods described in DE '630 include the conversion (preferably at 180–250 degrees Celsius) in the presence of hydrogen and of a rhodium catalyst of PDC to propylene, the dechlorination at normal temperatures of PDC to a mixture (9:1) of propylene and chloropropylene in the presence of a pure titanium catalyst, and the reductive dehalogenation with sodium sulfide and a phase transfer catalyst of chlorinated hydrocarbons to alkylenes. The production of alkylenes from halogenated phosphonate esters under the influence of sulfur and olefinating agents containing phosphorus is also described.

U.S. Pat. No. 3,892,818 to Scharfe et al. (Scharfe) describes processes for converting hydrocarbon chlorides including dichloropropane to hydrogen chloride and hydrocarbons, for example, mixtures of propane and propylene. The processes are conducted in the gas phase in the presence of rhodium-containing catalysts. Suitable catalysts are said to include carrier catalysts employing rhodium as a compound or as a metal, and while rhodium can be the sole catalytically active component of the carrier catalysts, other metals or metal compounds can be included such as, for example, palladium, platinum, ruthenium, iridium, iron, cobalt, nickel, copper, gold, vanadium, chromium, molybdenum and tungsten. Suitable carriers can be aluminum oxide, silicic acid, aluminum silicate, spinel, active charcoal and titanium dioxide, and can have inner surface areas anywhere from 1 to 500 m$^2$/g. The temperature of reaction can be from 50 to 500, especially 100 to 400, and most especially 150 to 350 degrees Celsius, and the reaction can be conducted at normal, reduced or elevated pressures.

U.S. Pat. Nos. 4,818,368 to Kalnes et al., 4,899,001 to Kalnes et al., and 5,013,424 to James, Jr. et al., while not appearing to address specifically the catalytic conversion of PDC, are similar to Scharfe in describing processes for the hydrogenation of halogenated hydrocarbons in the presence of metal or mixed metal catalysts, see, e.g., col. 7, line 30 to col. 8, line 2 of the '368 Kalnes et al. patent). "Hydrogenation" in these patents is contemplated as including dehalogenation and olefin saturation, see, e.g., col. 4, lines 41–47 of the '001 Kalnes et al. patent, col. 7, lines 6–11 of the '368 Kalnes et al. patent, and col. 9, lines 34–38 of the James, Jr. et al. patent.

German Patent Publications 3,510,034 A1 and 4,012,007 A1 describe the reductive dehalogenation of halohydrocarbons in the gas phase in the presence of an activated carbon, and embrace or exemplify the conversion of PDC to propylene. In the former publication, the reductant is an alkane, e.g., methane, propane, isobutane, cyclohexane, and the gas phase reaction is conducted at from 200 to 600 degrees Celsius. In the latter publication, halohydrocarbons and hydrogen are reacted in the gas phase at from 200 to 700 degrees Celsius.

SUMMARY OF THE INVENTION

The present invention provides a different route for catalytically converting a saturated halohydrocarbon to a corresponding non-halogenated, unsaturated hydrocarbon, the saturated halohydrocarbon and its corresponding non-halogenated, unsaturated hydrocarbon in a preferred embodiment being PDC and propylene, respectively.

By the present process, a saturated halohydrocarbon is reacted with hydrogen or a hydrogen donor in the gas phase in the presence of a catalytically effective amount of ruthenium on a support, and at temperatures of at least about 100 degrees Celsius, to produce reaction products including a corresponding non-halogenated, unsaturated hydrocarbon. In one particular application of the process, PDC is converted to reaction products including propylene.

An activated alumina-supported ruthenium catalyst is described (as among more than thirty other possible catalyst combinations) in U.S. Pat. No. 2,379,697 to Evans et al. for reducing vinyl-type halides to diolefins. An exemplary application is for reducing 2-chlorobutene-2 to butadiene. To applicants' knowledge, however, the use of a supported ruthenium catalyst for producing propylene from PDC (for example) has not been suggested.

DETAILED DESCRIPTION OF THE PREFERRED EMBODIMENTS

Figure 1:
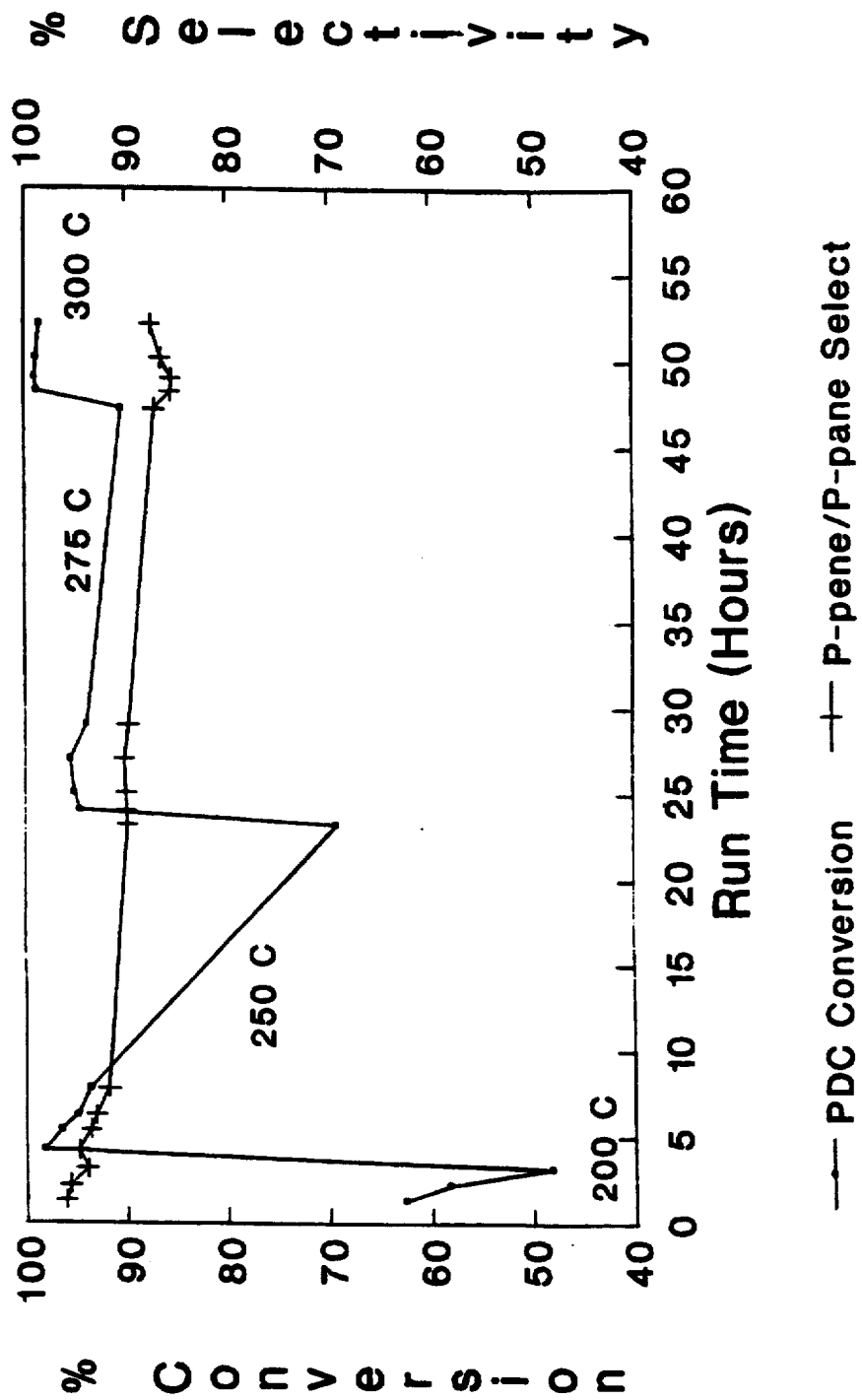
FIG. 1 graphically depicts the results of Example 1 below.

The supported ruthenium catalysts of the present invention will, when employed for making propylene from PDC, generally contain from about 0.01 to about 5 weight percent of ruthenium, although preferably the catalysts will contain from about 0.1 to about 1.0 percent by weight of ruthenium, and most preferably will contain about 0.5 percent by weight of ruthenium.

The support will preferably be alumina, and can have a specific surface area of between 10 and 350 square meters per gram, especially between 50 and 200 square meters per gram. The support more preferably will consist of a low specific surface area alumina, for example, an alumina having a surface area of between 90 and 110 square meters per gram (e.g., ⅛ inch diameter alumina pellets from Englehard Catalyst Division of Englehard Corporation). Other supports should also be useful, such as silica or carbon. Preparation of the catalyst will be by conventional methods. A particularly suitable, commercially available ruthenium on alumina catalyst is sold by Englehard Corporation under the designation 29024, and consists of 0.5 percent by weight of ruthenium on an alumina pellet (⅛ inch diameter) having a surface area of 90 m²/g.

The catalysts are preferably pretreated by drying under a nitrogen purge for 8 to 24 hours at 150 degrees Celsius, and then increasing the catalyst temperature to 250 degrees Celsius and reducing the catalyst with hydrogen for 24 hours.

A process for converting PDC to reaction products including propylene using the pretreated ruthenium catalysts of the present invention will preferably be conducted in the gas phase at pressures ranging from 0 up to about 1500 psig, preferably from 0 to about 100 psig, and most preferably at essentially atmospheric pressure, and will preferably react PDC with hydrogen to produce propylene along with hydrogen chloride and other materials such as propane, methane, and ethane. The temperature of reaction is generally from about 200 (100) degrees Celsius to about 350 degrees Celsius, although preferably the reaction will be conducted at from about 275 to about 300 degrees Celsius, and most preferably at about 300 degrees Celsius.

The molar feed ratio of hydrogen to PDC can vary over a significant range without selectively producing propane over propylene, but will preferably be from about 0.5:1 up to about 100:1, more preferably will range from about 2:1 to about 10:1, and most preferably will be about 5:1.

Residence times will preferably be between about 0.5 and about 20 seconds, more preferably will be from about 2 to about 6 seconds, and most preferably will be about 4 seconds.

The present invention is more fully and particularly illustrated by the examples which follow:

Illustrative Examples

In each of the following examples, a PDC to propylene conversion was obtained by the gas phase reaction of PDC and hydrogen over a commercially-available catalyst sold by Englehard Corporation (Seneca, S.C.) under the designation 29024, and having 0.5 percent by weight of ruthenium on a 90 m²/gram alumina support (⅛ inch diameter pellets). In each instance, liquid PDC was pumped via a high pressure syringe pump through 1/16 inch (O.D.) Monel TM nickel alloy tubing (unless specifically noted below all of the components, tubing and fittings of the test reactor apparatus were also made of Monel TM nickel alloy (Huntington Alloys, Inco Alloys International, Inc.)) into a packed sample cylinder serving as a feed evaporator.

The 1/16 inch tubing extended almost to the center of the packed cylinder, which was heated to a vaporizing temperature of 200 degrees Celsius using electrical heat tracing. Vaporization of the PDC was accomplished in the feed line, so that the PDC was superheated when combined with the hydrogen feed stream. Thermocouples were used to monitor the skin temperature of the feed evaporator and the temperature of the gas exiting the feed evaporator, and the temperature of the feed evaporator was manually controlled using a variable rheostat to control the power output to the electrical heat tracing.

The hydrogen feed stream was metered to a preheater using a Model 8249 linear flow mass controller from Matheson Gas Products, Inc. Secaucus, N.J., with the preheater consisting of a packed sample cylinder wrapped with electrical heat tracing. Thermocouples were used to monitor both the skin temperature of the preheater and the temperature of the gas exiting the preheater. The preheater temperature was manually set at 170 degrees Celsius using a variable rheostat to control power output to the electrical heat tracing.

Vaporized PDC exiting the evaporator was mixed with the hydrogen gas from the preheater in a 2 foot long section of ¼ inch tubing maintained at a temperature of 160 degrees Celsius. The mixed gases then were passed into and reacted within a tubular reactor (⅜ inch O.D., 4.5 inches in length) located within the oven compartment of a Hewlett Packard Model 5710A gas chromatograph. The chromatograph's temperature controller was used to vary the reaction temperature as needed or desired.

The 5 cubic centimeter charge of catalyst in the tubular reactor was generally placed in the tubular reactor over a glass wool support contained in the bottom of the reactor tubing. The catalyst was then covered with a plug of glass wool, and approximately 1 cubic centimeter of alumina (Harshaw 3996R grade, 10×20 mesh Harshaw/FILTROL, P.O. Box 22126, Beachwood, Ohio 44122) was added to serve as a guard bed. The remainder of the reactor was then packed with glass wool to minimize dead volume in the reactor.

Pretreating of the catalyst involved drying the catalyst for from 8 to 24 hours at 150 degrees Celsius under a nitrogen purge. The catalyst was thereafter reduced by passing hydrogen through the reactor at a flow rate of 34 ml/minute for 24 hours, and the reactor temperature was then lowered to the temperature setpoint of the particular catalyst run. The reactor temperature and hydrogen gas flow were allowed to equilibrate for about 1 hour before the liquid PDC was started into the apparatus.

After reacting the PDC and hydrogen in the tubular reactor thus prepared, the products from the reaction were sampled via a syringe sample port and 200 microliter syringe samples injected into a Hewlett Packard Model 5890—Series II gas chromatograph for analysis. The gas chromatograph (GC) was equipped with a flame ionization detector and a 50 meter by 0.32 mm (I.D.) methyl phenyl (5%) silicone/fused silica capillary column with a 1.0 micron film thickness. The initial oven temperature in this GC was 35 degrees Celsius, and after holding the sample at this temperature for 1 minute, the temperature was ramped to 200 degrees Celsius at a rate of 10 degrees Celsius per minute. The GC was then held at 200 degrees Celsius for a period of 3 minutes.

Response factors for the GC were conventionally calculated from microliter injections of gravimetrically prepared standards of the individual components (from Aldrich Chemical Co.) in carbon tetrachloride, and assuming a response factor of 1.0000 for 1,2-dichloroethane. These response factors were used in turn with the area counts of a component's peak and the total moles of all effluent components to determine the mole percent of each component present in the effluent. Selectivity to individual reaction products (e.g., propylene, propane, ethane, methane, chloropropenes) was determined by dividing the number of moles of a component produced in the reaction by the total number of moles of all product (organic) components (including unreacted PDC), and multiplying by 100.

A separate 100 microliter syringe sample was injected into a Hewlett Packard Model 5890 GC equipped with a cryogenic cooling accessory, to determine the ratio of propylene to propane present in the reactor effluent. The analytical column for this GC was a 60 meter by 0.32 mm (I.D.) methyl phenyl (1%) silicone/fused silica capillary column with a 1.0 micron film thickness. The initial oven temperature for the analysis was at $-30$ degrees Celsius, and after holding the sample at this temperature for 4.00 minutes, the temperature was ramped up to 200 degrees Celsius at a rate of 6 degrees Celsius per minute. The analysis was concluded after 5 minutes at the 200 degree temperature, with the propylene to propane ratio in the reactor effluent being determined by the area counts associated with each of the two materials (assuming equal response factors).

EXAMPLE 1

For this example, vaporized PDC and hydrogen were fed to the reactor at a molar ratio of 5 moles of hydrogen per mole of PDC, and were reacted initially at 200 degrees Celsius and with a 4 second residence time. As can be seen from FIG. 1, the PDC conversion (100-mole percent PDC in effluent) was low at this temperature, and the catalyst deactivation rapid. Increasing the reaction temperature to 250 deg. C. increased the conversion and slowed the rate of catalyst deactivation.

PDC conversion on further increasing the reaction temperature to 275 deg. C. was about 95 percent, and the rate of deactivation slowed dramatically. Selectivity to propylene and propane as reaction products was at 90 percent with a hydrogen to PDC molar feed ratio of 5:1, and the molar ratio of propylene to propane produced was about 3:1. After 48 hours of run time, PDC conversion had dropped from 95 to about 90 percent, and selectivity to propane and propylene on a molar basis dropped to about 87 percent. The molar ratio of propylene to propane had increased, however, from 3:1 to 7:1.

On increasing the reactor temperature to 300 degrees Celsius, PDC conversion was increased to 98 percent while selectivity to propylene and propane remained at about 87 percent. Propylene was preferentially produced to propane at a ratio of 8:1. The reactor temperature was held at 300 deg. C. for another 4.5 hours, with no loss in PDC conversion.

The temperature was then lowered to 250 deg. C., and the PDC conversion dropped immediately to about 40 percent although the propylene/propane ratio remained at about 8:1.

EXAMPLES 2-5

For these examples, the effects of residence time and the hydrogen to PDC molar feed ratio (at a reactor temperature of 250 deg. C.) on the propylene/propane product ratio were studied. The results of these runs are in Table 1:

| $H_2$:PDC Feed Ratio | Residence Time | $C_3H_6/C_3H_8$ Ratio |
| --- | --- | --- |
| 5:1 | 4 sec. | 8:1 |
| 5:1 | 11 sec. | 5:1 |
| 10:1 | 7 sec. | 2.5:1 |
| 3:1 | 9 sec. | 7:1 |

Table 1 suggests that lower residence times and lower hydrogen to PDC feed ratios should favor the production of propylene over propane.

EXAMPLE 6

This example focuses in greater detail and over a longer run time on the reaction at 300 deg. C. and a hydrogen to PDC molar feed ratio of 5:1.

Figure 2:
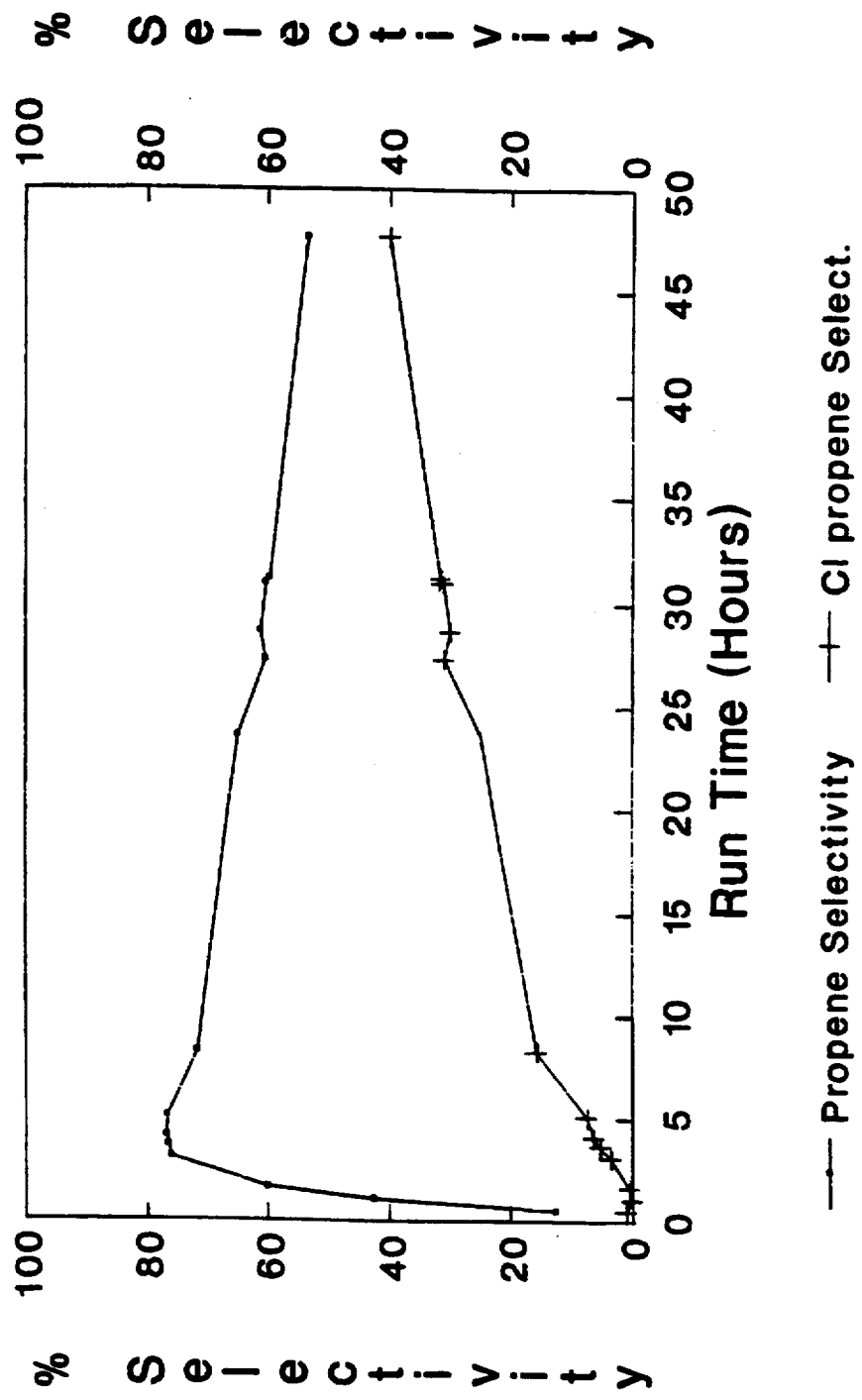
FIG. 2 graphically depicts the results of Example 6 below.

The selectivity to propylene under these conditions is shown graphically in FIG. 2 as a function of run time. Initial PDC conversion was greater than 99.9 percent, although the catalyst exhibited a break-in period wherein the selectivity to methane and ethane were very high and selectivity to propylene was about 40 percent.

After about 4 hours of use, the selectivity of the catalyst to methane and ethane had dropped to below 5 percent, while propylene selectivity increased to 75 percent. After 50 hours of use, PDC conversion remained at 99.5 percent, indicating a low catalyst deactivation rate. However, over the time frame from 4 hours to 50 hours, propylene selectivity dropped from 75 percent to 53 percent while selectivity to chloropropene as a reaction product increased from 5 percent to 40 percent.

It is expected however that by routine optimization of start-up and reaction conditions, e.g., hydrogen to PDC molar feed ratios, residence times, catalyst support and reactor temperature, the yield loss of propylene to chloropropene can be minimized.

What is claimed is:

1. A hydrodehalogenation process, comprising the step of reacting a saturated halohydrocarbon with hydrogen or a hydrogen donor in the presence of a catalyst which consists of ruthenium on a support and at temperatures of at least about 100 degrees Celsius, whereby one or more halogens are removed from the saturated halohydrocarbon to produce reaction products including a corresponding non-halogenated olefin.

2. A process as defined in claim 1, wherein the saturated halohydrocarbon is 1,2-dichloropropane, and wherein the 1,2-dichloropropane is converted to reaction products including propylene.

3. A process as defined in claim 2, wherein 1,2-dichloropropane is reacted with hydrogen in the gas phase at a pressure of from 0 to about 1500 psig and at a temperature from about 100 to about 350 degrees Celsius, and further wherein the catalyst contains from about 0.01 to about .5 weight percent of ruthenium.

4. A process as defined in claim 3, wherein the reaction is conducted at a pressure of from 0 to about 100 psig and a temperature of from about 275 to about 300 degrees Celsius, and further wherein the catalyst contains from about 0.1 to about 1.0 percent by weight of ruthenium.

5. A process as defined in claim 4, wherein the reaction is conducted at about atmospheric pressure and a temperature of about 300 degrees Celsius, and further wherein the catalyst contains about 0.5 percent by weight of ruthenium.

6. A process as defined in claim 3, wherein the molar feed ratio of hydrogen to 1,2-dichloropropane is from about 0.5:1 to about 100:1.

7. A process as defined in claim 4, wherein the molar feed ratio of hydrogen to 1,2-dichloropropane is from about 2:1 to about 10:1.

8. A process as defined in claim 5, wherein the molar feed ratio of hydrogen to 1,2-dichloropropane is about 5:1.

9. A process as defined in claim 6, wherein the residence time associated with said reaction is between about 0.5 and about 20 seconds.

10. A process as defined in claim 7, wherein the residence time associated with said reaction is between about 2 and about 6 seconds.

11. A process as defined in claim 8, wherein the residence time associated with said reaction is about 4 seconds.

12. A process as defined in claim 9, wherein the support is alumina having a specific surface area of between 10 and 350 square meters per gram.

13. A process as defined in claim 10, wherein the support is alumina having a specific surface area of between 50 and 200 square meters per gram.

14. A process as defined in claim 1, wherein the support is alumina having a specific surface area of between 90 and 110 square meters per gram.

* * * * *